United States Patent [19]
Reiner

[11] 4,283,126
[45] Aug. 11, 1981

[54] METHOD AND APPARATUS FOR EYE REFRACTION DETERMINATION

[75] Inventor: Josef Reiner, Cologne, Fed. Rep. of Germany

[73] Assignee: Herbert Schwind GmbH & Co. KG, Aschaffenburg, Fed. Rep. of Germany

[21] Appl. No.: 25,643

[22] Filed: Mar. 30, 1979

[30] Foreign Application Priority Data

Apr. 7, 1978 [DE] Fed. Rep. of Germany ....... 2815120

[51] Int. Cl.³ ............................................... A61B 3/02
[52] U.S. Cl. ........................................ 351/30; 351/29
[58] Field of Search .................. 351/6, 7, 13, 1, 16, 351/26, 27, 28, 29, 30, 17, 18

[56] References Cited

U.S. PATENT DOCUMENTS

| 3,524,702 | 8/1970 | Bellows et al. | 351/13 |
| 3,572,910 | 3/1971 | Koester | 351/30 |
| 3,737,217 | 6/1973 | Haines et al. | 351/13 |
| 3,904,280 | 9/1975 | Tate | 351/1 |

*Primary Examiner*—Conrad J. Clark
*Assistant Examiner*—Rodney B. Bovernick
*Attorney, Agent, or Firm*—Sprung, Felfe, Horn, Lynch & Kramer

[57] ABSTRACT

Method and apparatus for determining eye refraction using corrective lenses comprising projecting the corrective lens by means of an optical system into the pupil of the eye or in a predetermined spaced relation in front of said pupil, e.g., via a splitting mirror; this permits sight testing without the use of test spectacles and impairment of field of vision.

8 Claims, 3 Drawing Figures

METHOD AND APPARATUS FOR EYE REFRACTION DETERMINATION

This invention relates to a method and apparatus for determining eye refraction using test lenses.

In determining eye refraction using test lenses, the results obtainable are greatly dependent on the visual acuity, the faculty of observation and the power of communication of the test subject. Since during the refraction process the test subject is required either to put on relatively heavy test spectacles and look through test or corrective lenses with a relatively small diameter or through a phoroptor with corrective lenses of small diameter, these instruments are onerous in use during the course of the refraction determination and will irritate the subject owing to the limitation of his field of vision and due to any possible mirror images caused by a plurality of successive corrective lenses.

The instant invention provides a method and apparatus for making a refraction determination using test lenses where the test subject can observe the sight test without the use of test spectacles and without any restriction of his field of vision. This is accomplished by projecting the test lens, into the pupil of the eye, by means of an optical system or in a predetermined spaced relation in front of said pupil.

The apparatus for eye refraction determination of the invention comprises an interchangeable corrective element and a first imaging element which projects said corrective element toward the eye to be examined.

Further features and expedient developments of the invention can be seen from the description of embodiments with reference to the drawing in which.

Figure 1:
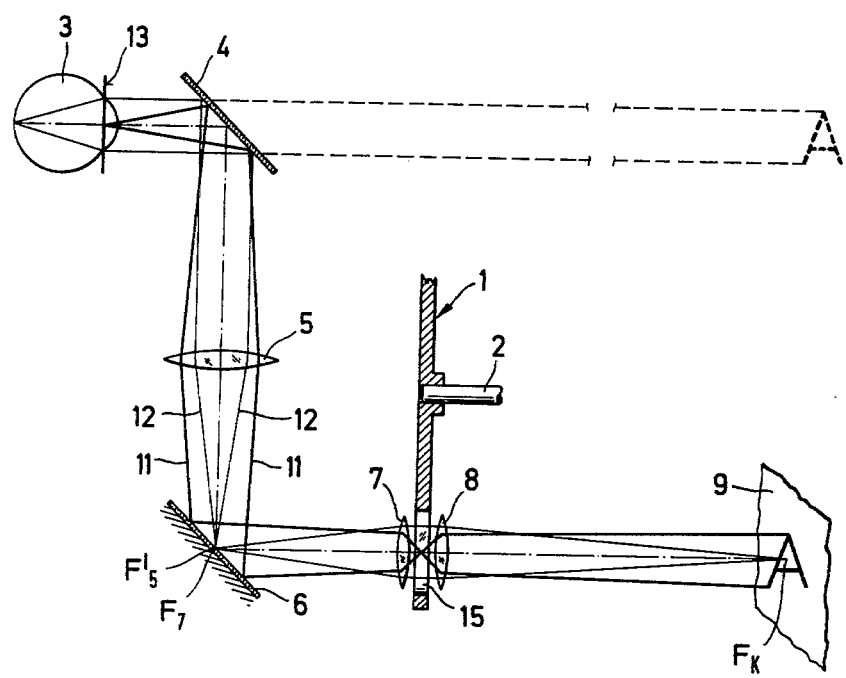
FIG. 1 shows the apparatus with a beam path for a person with normal sight.

The apparatus shown in FIG. 1 comprises a semi-transparent splitting mirror 4, a convex lens 5, a mirror 6 and a phoroptor 1 adapted to be pivotable about an axis 2, all of which are located in the beam path as seen from the entrance side facing the eye 3 to be examined. The phoroptor usually includes a plurality of corrective lenses of differing strengths which can be positioned in the beam path. In the setting shown in the illustration, the corrective effect of the lens 15 in the beam path is equal to zero. A collimator 8 for projecting optotypes 9, located upstream in the beam path, is provided in back of the phoroptor. A convex lens 7 is positioned in the beam path in front of the phoroptor and as close as possible thereto. The focal length of said convex lens is the same as that of the convex lens 5 interposed between the splitting mirror 4 and the mirror 6 and the object focal point $F_7$ thereof coincides with the image focal point $F_5'$. An optotype chart 9, reduced in size if desired, is positioned at the focal point $F_K$ of the collimator 8. The lenses, mirrors and the optotype chart are mounted in the apparatus by means of holders or mounts (not shown). The apparatus also includes a forehead support 10, shown in FIG. 3, which is adjustably connected to the housing in such a way that the eye to be examined of the test subject leaning against the forehead support assumes a predetermined keratometric distance from the convex lens 5.

The principal rays 11 in the beam path are illustrated by means of the thick solid lines and the secondary rays 12 are illustrated by means of the thin solid lines.

The lens of the phoroptor 1, which is located at approximately twice the focal length of the lens 5, is projected into the principal plane 13 of the eye 3 to be examined in the embodiment shown, but if desired can also be projected at a distance in front of the eye corresponding to the keratometric spacing of eyeglasses. The achieved effect is the same as if the test subject were looking through the corrective lens located in test spectacles or in a phoroptor positioned in front of the eye. The collimator 8, which is provided in back of the phoroptor, projects the optotypes located in the plane of focus thereof into infinity through the planar lens of the phoroptor and the two lenses 5 and 7, so that the eye 3 perceives the optotypes freely in space via the semi-transparent mirror 4.

Figure 2:
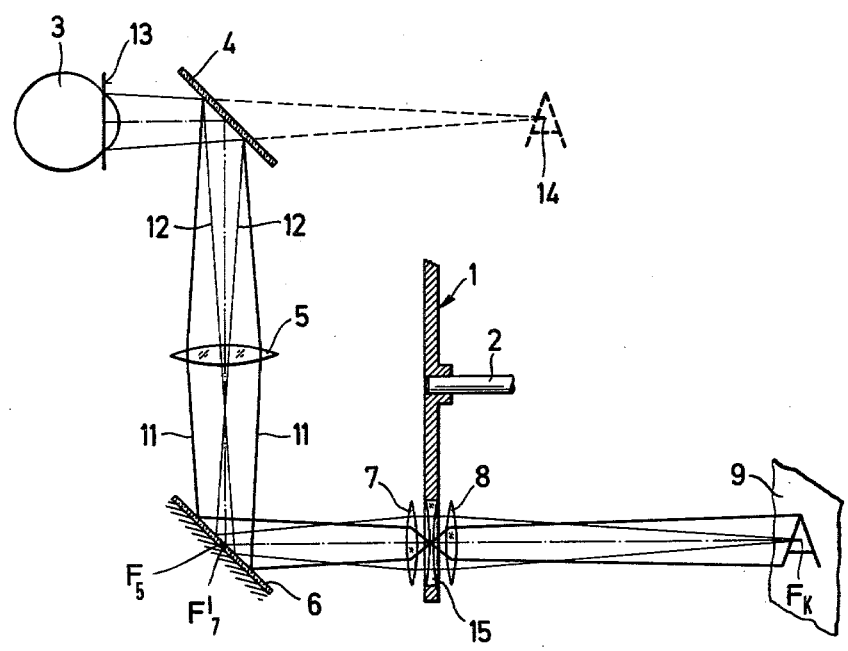
FIG. 2 shows the apparatus with a beam path for a myopic person.

FIG. 2 depicts the apparatus shown in FIG. 1 for examination of a myopic eye 3, the far-point 14 of which being located in spaced relation in front of the eye. The corrective lens 15 is again projected into the principal plane 13 of the eye to be examined via the two lenses 5 and 7. The conditions that the object focal point $F_5$ must coincide with the image focal point $F_7'$ of the lens 7 and that the lens 5 must be spaced from the corrective lens 15 of the phoroptor at a distance approximately equal to twice the focal length thereof ensure that the optotypes will be projected in the plane of the far-point 14 of the eye to be corrected. The same applies analogously to a presbyopic eye.

The use of the collimator 8 ensures that suitably reduced optotype charts such as 35 mm slides incorporating a plurality of optotypes can be employed in place of the large optotype charts employed heretofore.

Figure 3:
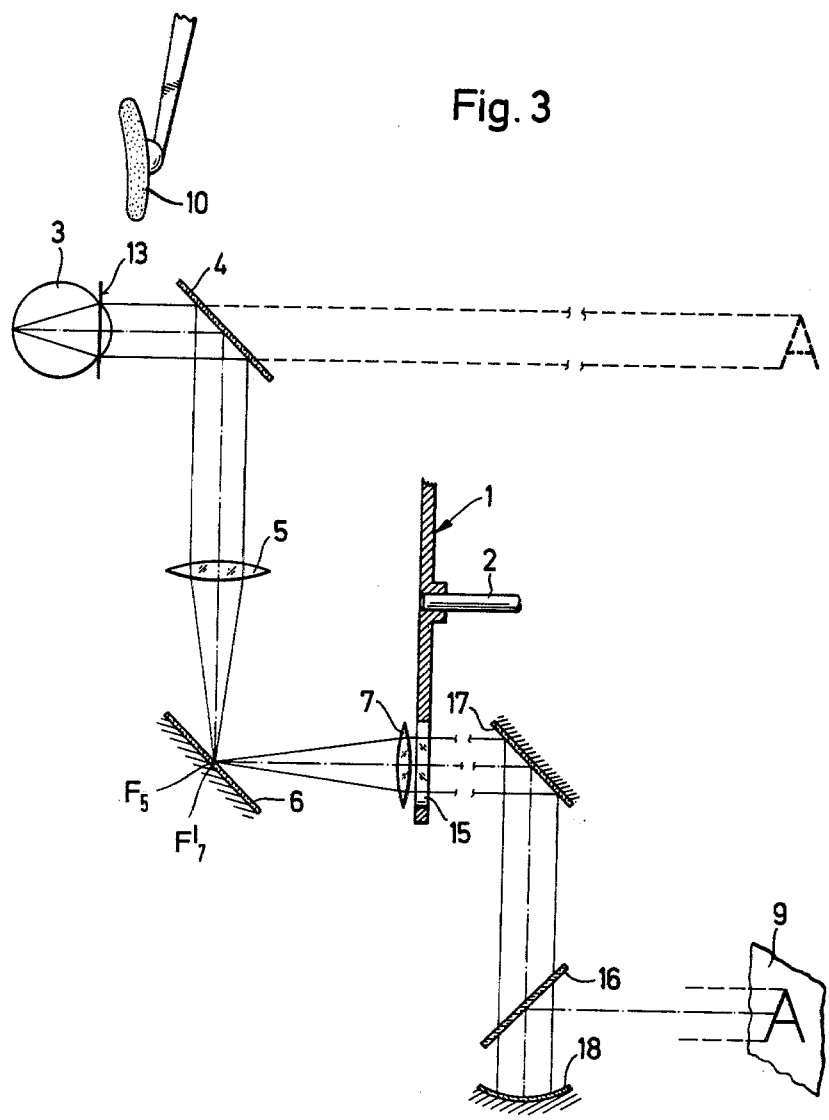
FIG. 3 shows an apparatus which has been modified as compared to the illustration in FIG. 1.

FIG. 3 illustrates an embodiment which differs merely in that a collimator mirror 18 is used instead of the collimator lens 8. The optotype chart 9 with the corresponding optotypes is again located in the focal plane of the collimator mirror. The optotype chart 9 is reflected via a semi-transparent splitting mirror 16 and a mirror 17 into the afore-mentioned beam path consisting of the phoroptor and the lenses 5, 7 as well as the semi-transparent mirror 4. This apparatus guarantees in all cases that the corrective lens of the phoroptor will constantly be projected to a desired distance from the eye and that the optotypes will be projected to the far-point of the eye to be corrected.

A universal test character can be used for binocular examination if a collimator lens or a collimator mirror is used whose diameter is larger than the interpupillar spacing. If two small lenses are used in front of the apertures of the phoroptor, two similar test figures must be used as in known stereoscopes.

The apparatus can also be used without the collimator 8 or the collimator consisting of elements 16, 17, 18 when the test indicia are presented at an adequate distance amounting, for instance, to 5 m by means of a cardboard chart on the wall in such a way that the test subject can see these test indicia through the semi-transparent mirror 4.

In the embodiments described hereinbefore, the focal lengths of the lenses 5 and 7 are equal and the principal plane 13 of the eye 3 is located at a position twice the focal length of lens 5. The corrective lenses of the phoroptor are therefore projected into the eye on a 1:1 scale. For this reason, the corrective lenses have the same effect as if they were located directly in front of the eye. For instance, if the patient requires a correction of −3.0 dpt, the corrective lenses 15 in the phoroptor must also be −3.0 dpt. The lateral amplification can be changed by varying the distance of the eye from the lens 5. If this amounts to 1:2, for instance, then the diopter value of the corrective lens 15 must be changed correspondingly. In this way the corrective lens 15 can be projected on a magnified scale if desired so that the corrective lenses can have a very large diameter and a large plurality of different lenses can thus be positioned on the phoroptor.

The apparatus is enclosed by a housing which has been omitted in the figure for purposes of clarification. The housing in turn includes the phoroptor 1, the lenses 5 and 7, the mirror 6 and, if desired, also the collimator including the optotype chart. An opening is provided above the lens 5 on the top of the housing above which is located the mirror 4. This is connected or fastened to the housing by means of a suitable mount. The impression of free spatial vision is achieved optimally by virtue of the fact that the mirror is not located inside the housing and the test subject thus does not have to look into the housing or apparatus, but simply looks through the semi-transparent mirror.

In the embodiment shown in FIG. 3, the distance between the optotypes and the mirror 18 amounts to 40 cm, between the mirror 17 and the phoroptor approximately 20 cm, between the lens 7 and the lens 5, approximately 30 cm and between the lens 5 and the eye also approximately 30 cm. The relatively large distance between the mirror 17 and the phoroptor ensures that other measuring components, for example cross-cylinders, can be externally introduced into the beam path. The housing can have a suitable opening for this purpose.

It will be understood that the specification and examples are illustrative but not limitative of the present invention and that other embodiments within the spirit and scope of the invention will suggest themselves to those skilled in the art.

What is claimed is:

1. A method for determining eye refraction using corrective lenses which method comprises spacing the corrective lens at a distance from the eye to be examined and projecting an image of the corrective lens into the pupil of the eye or at a predetermined spaced relation in front of said pupil by positioning at least one optical element including a beam splitter mirror in the light path between the corrective lens and the eye to be examined with the corrective lens positioned out of the line of vision of the eye to be examined to simulate the positioning of the corrective lens at the selected one of into or in front of the pupil and to simulate vision in free space by the eye to be examined of an optotype imaged on the corrective lens.

2. In an apparatus for determining eye refraction of the type wherein different corrective lenses are sequentially used for the determination, the improvement comprising means for mounting the corrective lenses at a distance spaced from the eye to be examined out of the line of sight of the eye to be examined and means for projecting an image of the corrective lens into the pupil of the eye or at a predetermined spaced relation in front of the pupil including at least one optical element comprising a beam splitter mirror in the light path between the corrective lens and the eye.

3. Apparatus as claimed in claim 2 wherein the projecting means includes two optical lenses between the corrective lens and the beam splitter mirror and wherein the image focal point of the one optical lens closer to the corrective lens coincides with the object focal point of the other optical lens.

4. Apparatus as claimed in claim 3 wherein the focal lengths of the two optical lenses are equal.

5. Apparatus as claimed in claim 3 wherein said corrective lenses are disposed substantially in the plane located at a distance of twice the focal length of said other optical lens from said other optical lens.

6. Apparatus as claimed in claim 3 wherein said projecting means further includes a collimator positioned in the beam path in front of said corrective lenses and optotypes in the focal plane of said collimator.

7. Apparatus as claimed in claim 6 wherein the focal length of said collimator is variable and capable of enlarging or magnifying the optotypes.

8. Apparatus as claimed in claim 2 further comprising a forehead support which is displaceably mounted to vary the distance between said eye to be examined and said beam splitter mirror.

* * * * *